(12) United States Patent
Cahill

(10) Patent No.: US 7,182,510 B2
(45) Date of Patent: Feb. 27, 2007

(54) APPARATUS AND METHOD FOR MEASURING THERMAL CONDUCTIVITY

(76) Inventor: David Gerard Cahill, 1728 County Rd. 500 East, Champaign, IL (US) 61822

( * ) Notice: Subject to any disclaimer, the term of this patent is extended or adjusted under 35 U.S.C. 154(b) by 38 days.

(21) Appl. No.: 11/103,660

(22) Filed: Apr. 4, 2005

(65) Prior Publication Data
US 2006/0222043 A1   Oct. 5, 2006

(51) Int. Cl.
G01K 25/18 (2006.01)
G01K 1/00 (2006.01)
G06F 17/00 (2006.01)

(52) U.S. Cl. .............................. 374/44; 374/120; 703/2

(58) Field of Classification Search ................ 374/4–7, 374/29–30, 43–44, 57, 208, 120, 135–136, 374/117, 119; 703/2
See application file for complete search history.

(56) References Cited

U.S. PATENT DOCUMENTS 4,521,118 A * 6/1985 Rosencwaig .................... 374/5
4,679,946 A * 7/1987 Rosencwaig et al. ........... 374/5
5,228,776 A * 7/1993 Smith et al. ..................... 374/5
6,054,868 A * 4/2000 Borden et al. ............... 324/752
6,422,741 B2 * 7/2002 Murphy et al. .................. 374/5
6,840,667 B2 * 1/2005 Schlagheck et al. ............ 374/5
6,971,791 B2 * 12/2005 Borden et al. ................... 374/5
7,059,766 B2 * 6/2006 Lemoine et al. ............. 374/161

FOREIGN PATENT DOCUMENTS

JP          06201620 A  *  7/1994

* cited by examiner

Primary Examiner—Gail Verbitsky

(57) ABSTRACT

An apparatus and method for measuring and mapping thermal conductivity and thermal diffusivity at micrometer scale resolution. The apparatus and method utilize a mode-locked femtosecond pulsed laser in a pump-probe configuration to analyze time-domain thermoreflectance of a specimen to evaluate its thermal conductivity in micro-scale, so that, if desired, an image of thermal conductivity distribution of micro-scale regions may be obtained therefrom. A multi-layer, complete three-dimensional model that takes into account the entire three-dimensional heat flow in cylindrical coordinates enables micro-scale measurements to be made at an accuracy of about 90% of well-accepted values.

10 Claims, 4 Drawing Sheets

APPARATUS AND METHOD FOR MEASURING THERMAL CONDUCTIVITY

FIELD OF THE INVENTION

The present invention relates generally to apparata and methods for measuring the thermal conductivity of a specimen, specifically, a metal, semiconductor, ceramic or polymer specimen. More specifically, the present invention relates to apparata and methods that utilize a mode-locked femtosecond pulsed laser in a pump-probe configuration to analyze time-domain thermoreflectance of a specimen to evaluate its thermal conductivity in the micro-scale, so that, if desired, an image of thermal conductivity distribution of micro-scale regions may be obtained therefrom.

BACKGROUND OF THE INVENTION

The laser flash method is well established and widely used for thermal conductivity measurements. The method requires a disk-shaped specimen having a thickness greater than 1 millimeter and a diameter typically of 10 millimeters. The method can only measure the average value of the disk-shaped specimen and is unsuitable for measurements of thermal conductivity of regions or features that are on the scale of micrometers. Such micro-scale measurements are important for microelectronics industries with miniaturized devices and for high throughput screening of micro-scale combinatorial libraries.

The apparatus and method disclosed by Baba et al. in U.S. Pat. No. 6,595,685B2 allow micro-scale measurements of thermal properties to be made. They use two continuum wave lasers. One laser serves as the pump beam and is used to heat the surface of the specimen with a sinusoidally modulated intensity. The other laser serves as the probe beam that detects the reflectivity of the specimen surface as a measure of the surface temperature. The two beams are focused on the same spot. Baba et al. analyze the data with only a two-layer model and one-dimensional heat flow without taking into account the interface effects. The method may work only for low thermal conductivity materials when the lateral heat flow and the interface effects are small. But, even for the low conductivity glass, the method is not accurate as demonstrated by the data shown in Table I of the aforementioned US patent. The thermal effusivity of glass varies from 30% too high to 50% too low depending on the thickness of the molybdenum film deposited for the measurements. For high thermal conductivity materials such as metals, the short time thermal response (on the order of 100 picoseconds) is critical for accurate thermal property assessment, but that time scale is not accessible with continuum wave lasers. Therefore, accuracy of the data obtained from the aforementioned method is poor.

Improved measurement accuracy is achieved by methods disclosed by Baba in U.S. Pat. No. 6,592,252B2 and by Taketoshi and Baba in U.S. patent application number U.S. 2003/0202556A1. Both embodiments use rear heating-front probing configuration, and thus may only be applied to thin films deposited on optically transparent substrates. Furthermore, the metal films have to be thick enough to be optically opaque but not too thick to keep the thermal pulse from arriving within the time-window (a few nanoseconds) of the apparatus. Therefore, these two apparata put severe constraints on the geometries of the materials that are to be measured. Both embodiments use a pump beam to heat the specimen from one side of the thin film and a probe beam to detect the temperature change from the opposite side. The two-sided approach is simpler in mathematical equations to evaluate the thermal properties; however, the alignment of the beams for the two-sided measurement is laborious and extremely difficult.

These current apparata and methods have significant drawbacks: 1) the one-sided method has poor accuracy; 2) the two-sided methods put severe constraints on the specimen geometries; and, 3) all the aforementioned methods are suitable to only limited types of materials such as low conductivity materials. Thus, there is a need for apparata and methods that allow measurements of thermal conductivity to be made more reliably, accurately, conveniently and easily. There is also a need for such apparata and methods to allow accurate and convenient measurements to be made of a broad range of materials including metals, ceramics and polymers. There is yet a further need for such apparata and methods to be able to measure thermal properties in the micro-scale. There is still a further need for such apparata and methods to perform measurements on both bulk specimens and thin film specimens without laborious sample preparation or system alignment.

SUMMARY OF THE INVENTION

Accordingly, the above-identified shortcomings of existing apparata and methods are overcome by embodiments of the present invention. This invention relates to apparata and method for accurate and micro-scale measurements of thermal properties, so that, if desired, an image of the distribution of thermal conductivity of micro-scale regions may be obtained therefrom. Embodiments of this invention comprise apparatus and method that require no laborious procedure or sample preparation, that are able to measure both bulk metallographic specimens and thin film specimens, that are able to measure thin film specimens on both opaque and transparent substrates, that are able to measure thin film specimens with a thickness greater than about thirty nanometers, that are able to measure specimens of both high and low thermal conductivity from metals to semiconductors to ceramics to polymers, that are able to measure thermal conductivity at a spatial resolution of better than five micrometers, that are able to measure the thermal conductivity at a very high accuracy within ten percent variation from well-accepted handbook values. The embodiments of the apparatus and method of this invention allow measurements of thermal conductivity to be made more reliably, accurately, conveniently and easily than currently possible. Embodiments of this invention allow images of thermal conductivity to be collected from specimens conveniently to show the distribution or variation in the micro-scale. Furthermore, embodiments of this invention can be designed so they are used to perform high throughput measurements of combinatorial specimens to aid the discovery of new materials such as, but not limited to, thermoelectric materials and thermal barrier coatings. Finally, embodiments of this invention may serve as a research tool to examine the dependence of thermal conductivity on composition and phases, to study order-disorder transitions, and to study site preference of chemical elements in intermetallic compounds.

Several key embodiments of the present invention enable very accurate measurements of thermal conductivity at micrometer-scale resolution and at a very high measurement speed. Firstly, a transducer film such as a thin Al film is deposited onto a specimen to serve as a transducer to absorb laser pulses and enable sensitive measurements of the temperature change through the relatively large thermoreflectance of the transducer film at the wavelength range of about 740 to about 840 nanometers. Secondly, a mode-locked pulsed laser in the femtosecond frequency range is employed. The laser beam is split into two beams, the pump/heat beam and the probe beam. The pump beam is used to heat the near surface region of the transducer film and the probe beam to sense the thermoreflectance of the transducer film. As the heat diffuses through the transducer film to the specimen, the surface temperature of the transducer film decays and so does reflectivity of the transducer film, which is monitored by the probe beam. By varying the time delay between the pump beam and the probe beam, it is possible to access to the short time thermal response (on the order of 100 picoseconds) that is not accessible with the continuous wave lasers. Thirdly, the pump beam is modulated at about 10 MHz to limit lateral heat flow and the probe beam is modulated at audio frequencies to eliminate artifacts created by scattering of the pump beam by surface roughness. The selection of these modulation frequencies make the measurements more reliable. Fourthly, a new, more accurate thermal model that takes into account the entire three-dimensional heat flow in cylindrical coordinates and takes into account a minimum of three layers (the transducer film, the interface between the specimen and the transducer film, and the specimen) enables more accurate thermal conductivity data extraction. Lastly, the thermal effusivity, the square root of the product of the thermal conductivity, $\Lambda$, and heat capacity per unit volume, C, is extracted from the ratio of in-phase to out-of-phase voltage of the rf lock-in amplifier, $V_{in}(t)/V_{out}(t)$, at the modulation frequency of the pump beam. The thermal properties of the specimen are evaluated by matching the temperature decay obtained from experiment with that calculated from heat flow models. The use of $V_{in}(t)/V_{out}(t)$ is much more reliable and robust than the phase lag of a continuous wave probe beam, $V_{in}(t)$, $V_{out}(t)$ (without taking the ratio), or the relative intensity of the probe beam to the pump beam. These embodiments together with other embodiments of this invention make it possible to perform micro-scale measurements at about 3.5 micrometer resolution, ninety percent accuracy relative to the well accepted values, and a speed of more than 10,000 measurements per hour in mapping.

The embodiments of the present invention use a front heating—front sensing, one-sided approach which makes it possible to make measurements conveniently on both bulk specimens and thin film specimens. The thin film specimen can be on any substrate, opaque or transparent, either metallic, semiconductor, ceramic, or polymeric. The thickness of the thin film specimen can be as thin as about 30 nanometers. The embodiments of the present invention, especially the new, more reliable thermal model enable measurements to be made as accurately as or even more accurately than the two-sided approach that is very difficult to perform and too restrictive in specimen geometry.

In one embodiment of this invention, a specimen is mounted onto a X-Y translation stage such that data could be collected to produce an image of thermal conductivity to show the micro-scale distribution and variation of the thermal properties in two dimensions. Other embodiments of this invention comprise an apparatus and method for characterizing combinatorial specimens having multiple compositions on a chip or compositional variations in diffusion couples and diffusion multiples.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

Figure 1:
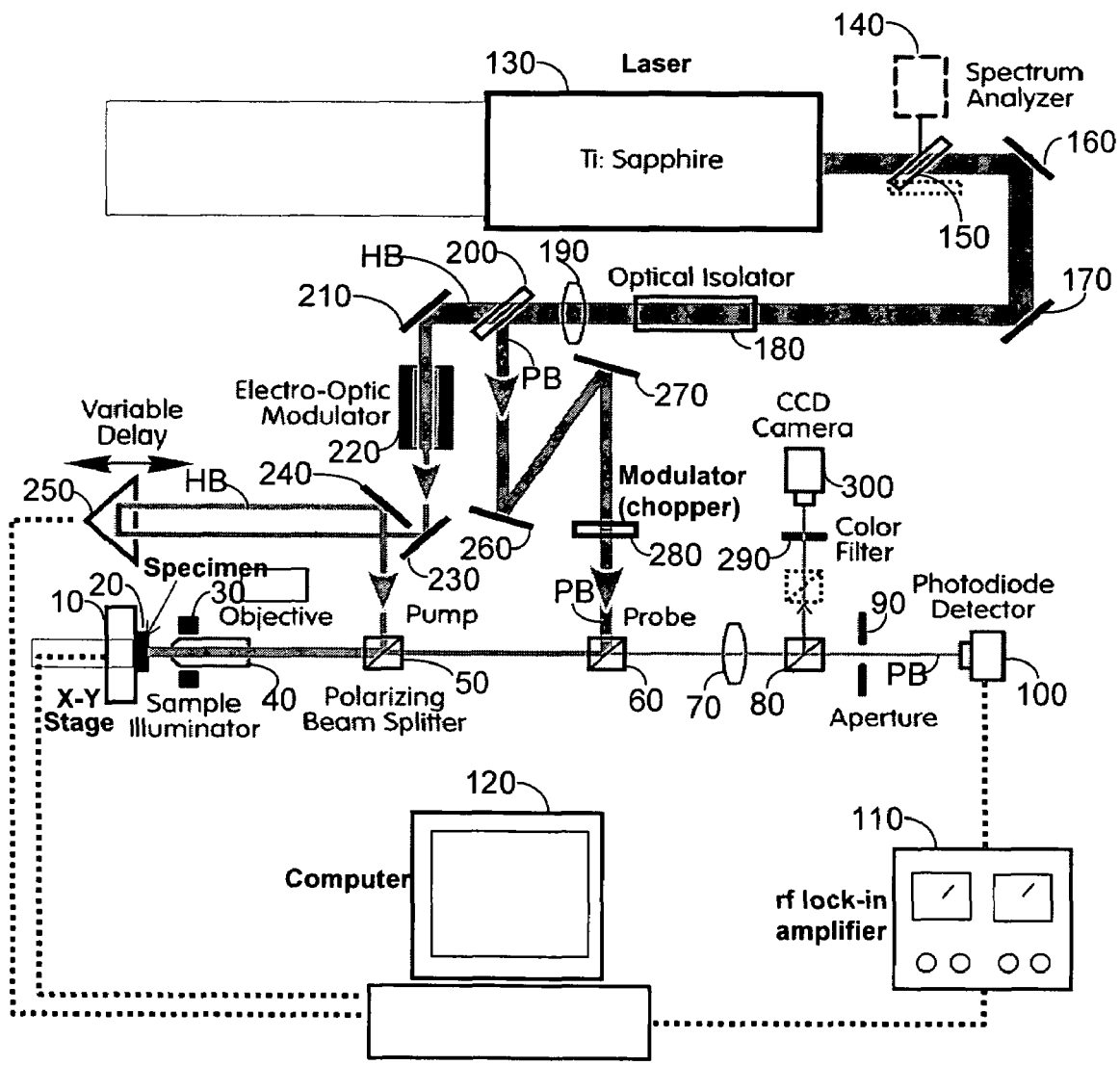
FIG. 1 is a block diagram showing an apparatus for carrying out the micro-scale thermal conductivity measurements using the embodiments of the present invention.
Figure 2A:
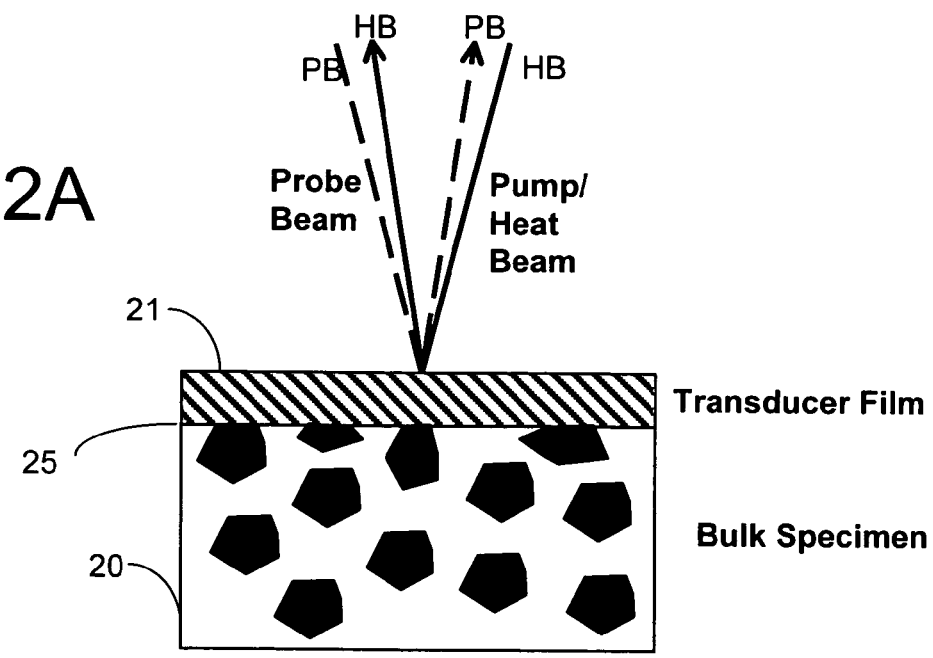
FIG. 2A and FIG. 2B are schematic diagrams showing the measurements of both a bulk specimen and a thin film specimen using the embodiments of the present invention.
Figure 2B:
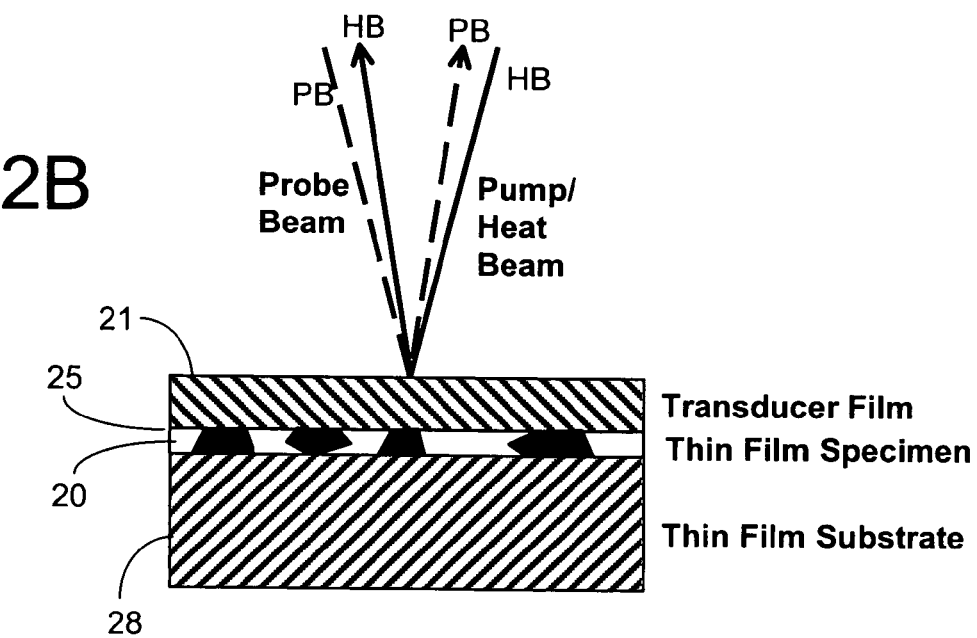

For the purposes of promoting an understanding of the invention, reference will now be made to some preferred embodiments of the present invention as illustrated in FIGS. 1 and 2, and specific language used to describe the same. The terminology used herein is for the purpose of description, not limitation. Specific components and their functional details disclosed herein are not to be interpreted as limiting, but merely as a basis for the claims as a representative basis for teaching one skilled in the art to various employments of the present invention. Any modifications or variations in the depicted apparatus and method, and such further applications of the principles of the invention as illustrated herein, as would normally occur to one skilled in the art, are considered to be within the spirit of this invention.

The present invention comprises a method for thermal conductivity measurements in micro-scale. The method comprises:

1) providing a specimen 20, the said specimen may be a metal, a semiconductor, a ceramic, or a polymer, or a combination thereof, and the said specimen may be a bulk specimen or a thin film specimen;

2) depositing a transducer thin film 21 onto a surface of the said specimen, the said transducer thin film 21 may have a thickness of about 50 to about 300 nanometers and preferably about 50 to about 150 nanometers, the said transducer film may be aluminum, ruthenium, and other metals, and preferably aluminum for measurements at temperatures less than 300 degrees Celsius, the said transducer film absorbs the energy of a pulsed laser beam HB and serves as a sensor of the temperature through its high dependency of reflectance on temperature, and the said transducer film 21 may be deposited using methods known in the art such as, but not limited to, sputtering;

3) providing a pulsed laser 130, the said laser has a wavelength in the range of about 740 to about 840 nanometer, preferably has a wavelength of about 770 nanometer;
4) providing a beam splitter 200, the said beam splitter separates the said pulsed laser into two beams: the pump/heat beam HB and the probe beam PB;
5) providing a modulator 220 to modulate the said pump beam HB into a frequency (f) in the range of 10 kHz to 20 MHz, preferably to a frequency of about 10 MHz to limit the heat penetration depth, and the said modulator 220 is preferably an electro-optic modulator;
6) providing a variable delay 250 for the said pump beam HB, the said variable delay 250 may be achieved by forcing the pump beam HB to go through an optical delay line to vary the length of the travel path using a retroreflector with a movable corner cube mirror or prism, and the said delay time (t) may vary from −100 to 10000 picoseconds, preferably about −100 to 4000 picoseconds;
7) providing an objective lens 40 to focus the said pump beam HB onto a spot on the surface of the said transducer film 21 on the said specimen 20, the said pump beam HB heats the near surface layer of the said transducer film 21, the temperature at the surface of the said transducer film 21 decays as the heat is conducted through the transducer film 21 to the specimen 20;
8) providing a modulator 280 to modulate the frequency of the aforementioned probe beam PB to the range of 10 to 1000 Hz, preferably to a frequency (F) of about 200 Hz to eliminate artifacts created by scattering of the pump beam HB by surface roughness, the said modulator 280 is preferably a mechanical beam chopper;
9) focusing the said probe beam PB on the same spot as the said pump beam HB on the transducer film 21, the said probe beam PB is reflected from the said transducer film 21 and travels through a series of beam splitters 50, 60 and 80, a focus lens 70, and an aperture 90 to reach a photodiode detector 100;
10) providing a photodiode detector 100 to convert the light signal into electrical signal;
11) providing a radio frequency (rf) lock-in amplifier 110 to detect the signal from said pump beam modulation frequency f, the said rf lock-in amplifier 110 produces in-phase output voltage $V_{in}(t)$ and out-of-phase voltage $V_{out}(t)$ that are dependent on the delay time t. The output signals of the rf lock-in amplifier appear at the modulation frequency F of the probe beam and are measured using two audio frequency lock-in amplifiers incorporated into the computer used for data acquisition.
12) providing a thermal model to calculate the heat evolution in the transducer film 21, the interface 25 between the transducer film 21 and the specimen 20, and the specimen 20, the said model takes into account the entire three-dimensional heat flow in cylindrical coordinates and takes into account a minimum of three layers (transducer film 21, interface 25, and specimen 20), the said model relates the ratio of in-phase output and out-of-phase output, $V_{in}(t)/V_{out}(t)$, to the delay time t and the thermal conductivity Λ, and the said model has been disclosed in detail in recent publications by Huxtable, Cahill, Fauconnier, White and Zhao in Nature Materials, volume 3, pages 298–301, May 2004, and by Cahill in Review of Scientific Instruments, volume 75, pages 5119–5122, December 2004;
13) providing a minimum of one computer 120 to control the variable delay 250, the rf lock-in amplifier 110, and an optional X-Y translation stage 10, and to perform data aquisition, modeling fitting, and data extraction;
14) performing experiments with varying delay time t and collecting $V_{in}(t)/V_{out}(t)$ data, fitting the thermal model equations with two free parameters: thermal conductivity Λ and the interface conductance G between the transducer film 21 and the unknown specimen 20 under test, and obtaining both Λ and the interface conductance G., based on the data, plot a curve of $V_{in}(t)/V_{out}(t)$ against thermal conductivity Λ.

One further embodiment of this invention comprises a method for thermal conductivity measurements in micro-scale to allow quantitative image of thermal conductivity to be taken. The method further comprises:

15) providing a X-Y translation stage 10 to move the sample at micrometer steps relative to the focused laser beams HB and PB;
16) selecting an appropriate aforementioned delay time t such that the $V_{in}(t)/V_{out}(t)$ is only weakly dependent on the interface conductance G or the thermal conductivity of the transducer film and such that the $V_{in}(t)/V_{out}(t)$ scales approximately as the the effusivity $(\Lambda C)^{1/2}$ of the sample wherein the C is the heat capacity per unit volume of the specimen;
17) moving the specimen 20 in micrometer scale steps with respect to the aforementioned pump-probe focused spot, collecting the $V_{in}(t)/V_{out}(t)$ data, and calculating the thermal conductivity of each pixel from the said $V_{in}(t)/V_{out}(t)$ vs thermal conductivity curve;
18) generating a quantitative thermal conductivity image from the thermal conductivity data from each pixel.

The present invention comprises an apparatus for thermal conductivity measurements in micro-scale. The apparatus comprises:

1) a mode-locked pulsed laser 130, the said laser has a wavelength between about 740 and about 840 nanometer, the said laser 130 preferably has a wavelength of 770 nanometer, and the said laser is preferably a Ti:sapphire laser with femtosecond pulses;
2) an optical isolator 180 to prevent the reflected laser beam from returning into the said Ti:sapphire laser source;
3) a beam splitter 200, the said beam splitter 200 separates the said pulsed laser into two beams: the pump/heat beam HB and the probe beam PB, alternatively, two independent lasers may be used as the pump beam and the probe beam without the employment of the said beam splitter;
4) a modulator 220 to modulate the said pump beam HB into a frequency (f) in the range of 10 kHz to 20 MHz, preferably to a frequency of about 10 MHz, and the said modulator 220 is preferably an electro-optic modulator;
5) a variable delay mechanism 250 for the said pump beam HB, the said variable delay mechanism 250 is preferably a retroreflector with a corner-cube mirror or movable prism, and the said variable delay mechanism can produce a delay time (t) varying from −100 to 10000 picoseconds, preferably about −100 to 4000 picoseconds;
6) an objective lens 40 to focus the said pump beam HB onto a spot on the surface of the said transducer film 21 on the said specimen 20;
7) a modulator 280 to modulate the frequency of the aforementioned probe beam PB to the range of 10 to 1000 Hz, preferably to a frequency (F) of about 200 Hz, the said modulator 280 is preferably a mechanical beam chopper;
8) a polarizing beam splitter 50 that allows only the reflected probe beam PB to pass through it;
9) a photodiode detector 100 to convert the light signal into electrical signal;
10) a rf lock-in amplifier 110 to detect the signal from said pump beam modulation frequency f, the said rf lock-in amplifier 110 produces in-phase output voltage $V_{in}(t)$ and out-of-phase voltage $V_{out}(t)$ that are dependent on the delay time t. The output signals of the rf lockin-amplifier appear at the modulation frequency F of the probe beam and are measured using two audio frequency lock-ins incorporated into the computer used for data acquisition.

11) a minimum of one computer 120, the said computer 120 controls the variable delay 250, the rf lock-in amplifier 110, and an optional X-Y translation stage 10, the said computer 120 is used to perform data aquisition, modeling fitting, and data extraction, the said computer 120 has an executive software that embodies the aforementioned thermal model that takes into account the entire three-dimensional heat flow in cylindrical coordinates and takes into account a minimum of three layers (the transducer film 21, the interface 25 between the specimen 20 and the transducer film 21, and the specimen 20), the said model relates the ratio of in-phase output and out-of-phase output, $V_{in}(t)/V_{out}(t)$, to the delay time t and the thermal conductivity $\Lambda$, and the said model has been disclosed in detail in recent publications by Huxtable, Cahill, Fauconnier, White and Zhao in Nature Materials, volume 3, pages 298–301, May 2004, and by Cahill in Review of Scientific Instruments, volume 75, pages 5119–5122, December 2004.

One embodiment of this invention comprises an apparatus for thermal conductivity measurements in micro-scale to allow quantitative image of thermal conductivity to be taken. The apparatus further comprises a X-Y translation stage 10 to move the sample at micrometer steps relative to the focused laser beams HB and PB.

One further embodiment of this invention may comprise a series of mirrors 160, 170, 210, 230, and 240, beam splitting cubes 60 and 80, lenses 190 and 70, an aperture 90, one or more color filters 290, a sample illuminator 30, and a CCD camera 300 to direct the laser beams or to help find the desired locations on the specimen 20. These are all well known to those skilled in the art.

Figure 3A:
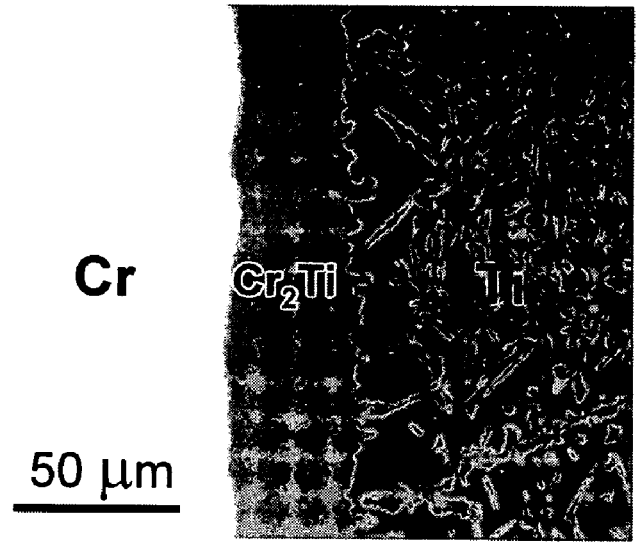
FIG. 3A is a scanning electron microscopy (SEM) micrograph of a Cr—Ti diffusion couple region of a sample, showing the Laves phase $Cr_2Ti$ in the middle and the Laves phase precipitates in the Ti rich compositions (right-hand side); and, FIG. 3B is a thermal conductivity image of the same region showing in FIG. 5A showing the capability of the apparatus and method of the present invention in obtaining an image to show thermal conductivity distribution in micro-scale.
Figure 3B:
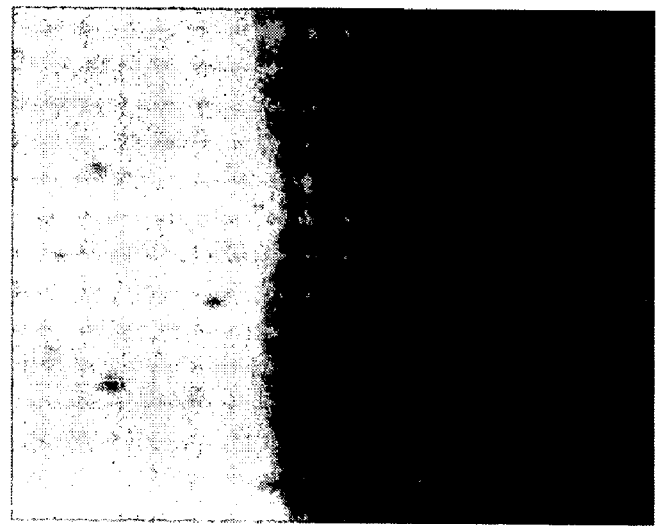

In order to verify that the developed thermal conductivity measurement apparatus and method are able to achieve micrometer scale resolution and high accuracy, an actual apparatus was made and it was employed to perform measurements on a diffusion multiple specimen and several other metallographic specimens. FIG. 3A shows a scanning electron microscopy (SEM) image of a cross-section of a Cr—Ti diffusion couple. The left-hand side of specimen consists of a Cr-based body-centered-cubic phase. In the middle of FIG. 3A, a $Cr_2Ti$ has formed, and on the right-hand side of the specimen, there are $Cr_2Ti$ precipitates in the Ti-rich body-centered-cubic phase. The specimen is first coated with a transducer film of pure aluminum of about 120 nanometers in thickness using sputtering. By scanning the sample at fixed delay time t of about 100 picosconds, and recording the values of $V_{in}(t)/V_{out}(t)$ at each pixel, a scanning image of the thermal effusivity of the sample is obtained. As all of the materials considered here have heat capacities within 20% of 2.7 J $cm^{-3}K^{-1}$, the effusivity data was divided by a constant $C_0=2.7$ J $cm^{-3}K^{-1}$ to create an image with units of thermal conductivity as shown in FIG. 3B. If thermal conductivity $\Lambda$ of a particular phase is desired, the exact value of $C_0$ can be taken from the literature (if known) or estimated from the atomic densities and Debye temperatures of the constituent elements. The deviations from the classical limit of 3 $k_B$ (where $k_B$ is Boltzmann's constant) per atom are relatively small; for example, Cr has the relatively high Debye temperature of 630 K, and the heat capacity of Cr at room temperature is 2.81 $k_B$ per atom. Each pixel in the thermal conductivity image shown in FIG. 3B contains quantitative data of thermal conductivity at the location. The spatial resolution of the measured implemented with the current invention is about 3.5 micrometers. The whole 100 by 100 pixel (a total of 10,000 pixels) image is obtained in an hour.

Figure 4:
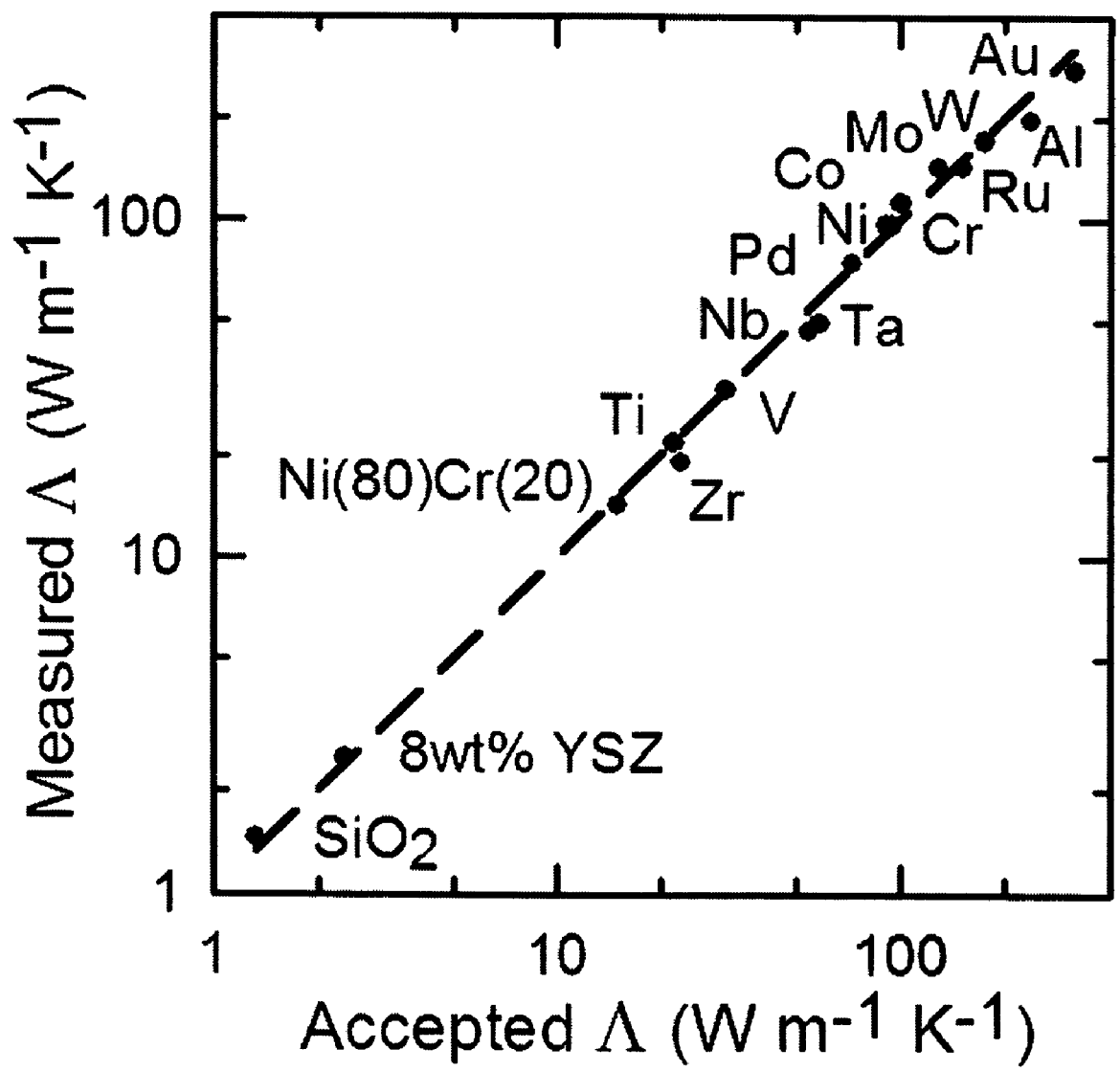
FIG. 4 is a plot of thermal conductivity values obtained from the apparatus and method implemented with the present invention against the well accepted handbook values of several metals and ceramic specimens showing very high accuracy of the apparatus and method of the present invention.

To further demonstrate the accuracy of the apparatus and the method of the present invention, several metals and ceramic specimens with well-known thermal conductivity values are tested using the apparatus and method implemented with the present invention as schematically shown in FIG. 1. The data obtained with the new apparatus and method are compared with the well-accepted values in FIG. 4. The excellent agreement attests the high accuracy of the present invention in micro-scale thermal conductivity measurements. FIGS. 3 and 4 clearly show that the apparatus and method of the present invention has achieved a combined high accuracy, high spatial resolution, and fast measurement speed that have never been demonstrated before in prior art.

Since the thermal diffusivity and thermal effusivity are related to the thermal conductivity with specific heat of the material, the apparatus and method of the present invention is equally suited for measurements and mapping of the thermal diffusivity and thermal effusivity. As a matter of fact, the direct data from the measurements were thermal effusivity.

Various embodiments of the invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. It is intended that the present invention cover all suitable modifications and variations as come within the scope of the appended claims and their equivalents.

What is claimed is:

1. A method for measuring the thermal conductivity on micrometer length scales, the method comprising:

depositing a transducer film onto a specimen;

providing a mode-locked femtosecond pulsed laser, said laser has a wavelength in the range of about 740 to about 840 nanometers;

providing a beam splitter, said beam splitter separates said pulsed laser beam into the pump beam and the probe beam;

providing a modulator to modulate said pump beam to a frequency in the range of 10 kHz to 20 MHz;

providing a variable delay mechanism for said pump beam, said variable delay mechanism can produce a delay time (t) from 100 to 10000 picoseconds;

focusing said pump beam onto a spot on the surface of said transducer film on said specimen, said pump beam heats the near surface layer of said transducer film, the temperature at the surface of said transducer film decays as the heat is conducted through the transducer film to the specimen;

providing a modulator to modulate the frequency of the aforementioned probe beam to the range of 10 to 1000 Hz;

focusing said probe beam on the same spot on the transducer film as said pump beam, said probe beam is reflected from said transducer film and directed to a photodiode detector;

providing a rf lock-in amplifier to detect the signal from the modulation frequencies of said pump beam, said rf lock-in amplifier produces in-phase output voltage Via (t) and out-of-phase voltage Vout (t) that are dependent on the delay time t;

providing a mathematical thermal model to calculate the heat conduction in the transducer film, the interface between the transducer film and the specimen, and the specimen, said model takes into account the heat flow in a minimum of three layers:

said transducer film, said interface, and said specimen, and said model relates the ratio of in-phase output and out-of-phase output, Vin (t)/ Vout (t), to the delay time t and the thermal conductivity;

performing experiments with varying delay time t and collecting Vin (t)/ Vout (t) data, and fitting the thermal model equations with two free parameters: thermal conductivity and the interface conductance G between the transducer film and the unknown specimen under test, and obtaining both the thermal conductivity and the interface conductance.

2. The method of claim 1, wherein the measurement is made for thermal diffusivity.

3. The method of claim 1, wherein said transducer film is selected from aluminum or ruthenium.

4. The method of claim 1, wherein said transducer film has a thickness about 50 to 200 nanometers.

5. The method of claim 1, further comprising:

providing a X-Y translation stage to move the sample relative to the spot of said pump beam and the said probe beam;

selecting an appropriate aforementioned delay time t such that the Vin (t)/ Vout (t) is only weakly dependent on the interface conductance G or the thermal conductivity of the transducer film;

moving the specimen with respect to the focused spot of both pump beam and the probe beam, collecting the Vin (t)/ Vout (t) data, and calculating the thermal conductivity of each pixel from the said Vin (t)/ Vout (t) vs thermal conductivity curve;

generating a quantitative thermal conductivity image from the thermal conductivity data from each pixel.

6. An apparatus for measuring the thermal conductivity in micrometer scale, the apparatus comprising:

a mode-locked pulsed laser, said laser has a wavelength between about 740 and about 840 nanometer;

a beam splitter, said beam splitter separates said pulsed laser into two beams: the pump/heat beam and the probe beam;

a modulator to modulate said pump beam into a frequency in the range of 10 kHz to 20 MHz;

a variable delay mechanism for said pump beam, said variable delay mechanism could produce a delay time (t) varying from 100 to 10000 picoseconds;

an objective lens to focus the said pump beam onto a spot on the surface of said transducer film on the said specimen;

a modulator to modulate the frequency of the probe beam to the range of 10 to 1000 Hz, said probe beam is focused on the same spot on the transducer thin film as the pump beam;

a rf lock-in amplifier to detect the signal from the modulation frequencies of said pump beam, said rf lock-in amplifier produces in-phase output voltage Vin (t) and out-of-phase voltage Vout (t) that are dependent on the delay time t;

a minimum of one computer, said computer has an executive software that embodies the aforementioned thermal model that takes into account the heat flow in a minimum of three layers: the transducer film, the interface between the specimen and the transducer film, and the specimen, said model relates the ratio of in-phase output and out-of-phase output, Vin (t)/ Vout (t), to the delay time t and the thermal conductivity.

7. The apparatus of claim 3, wherein the measurement is made for thermal diffusivity.

8. The apparatus of claim 3, wherein said transducer film is selected from aluminum or ruthenium.

9. The apparatus of claim 3, wherein said transducer film has a thickness about 50 to 200 nanometers.

10. The apparatus of claim 3, further comprising a X-Y translation stage to move the specimen relative to both the focused pump and probe beams;

Said X-Y stage allows quantitative image of thermal conductivity to be taken.

* * * * *